United States Patent
Novak (12)

(10) Patent No.: US 6,420,181 B1
(45) Date of Patent: *Jul. 16, 2002

(54) FIELD MICROSPOT TEST METHOD FOR ON-SITE CHEMICAL TESTING

(75) Inventor: Thaddeus John Novak, Bel Air, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/296,602

(22) Filed: Apr. 23, 1999

Related U.S. Application Data

(63) Continuation-in-part of application No. 08/763,181, filed on Dec. 11, 1996, now Pat. No. 5,935,862.

(51) Int. Cl.[7] .......................... G01N 33/00; G01N 30/90
(52) U.S. Cl. ....................... 436/104; 436/162; 436/164; 436/166; 436/169; 210/658
(58) Field of Search ................... 210/656, 658, 210/634, 635; 422/56, 58, 61, 68.1, 70; 436/103–105, 161–164, 166, 169, 808

(56) References Cited

U.S. PATENT DOCUMENTS 4,346,001 A * 8/1982 Tyihak et al. ............... 210/658
4,428,908 A * 1/1984 Ashley et al. ................ 422/61

* cited by examiner

*Primary Examiner*—Lyle A. Alexander
(74) *Attorney, Agent, or Firm*—Ulysses John Biffoni; William W. Randolph

(57) ABSTRACT

A method, system and kit for detecting the presence of an analyte includes placing a solution containing the analyte in a microcapillary tube and placing the microcapillary tube in contact with a layer of sorbent material so that the solution is withdrawn from the microcapillary tube by capillary action. The sorbent material and solvent for the solution are selected so that the solvent is absorbed into the sorbent material and the analyte is adsorbed by the sorbent material and concentrated at the spot where the microcapillary tube contacts the sorbent material. A detector reagent is applied to the sorbent material to indicate the presence of the analyte.

16 Claims, 2 Drawing Sheets

FIG.1
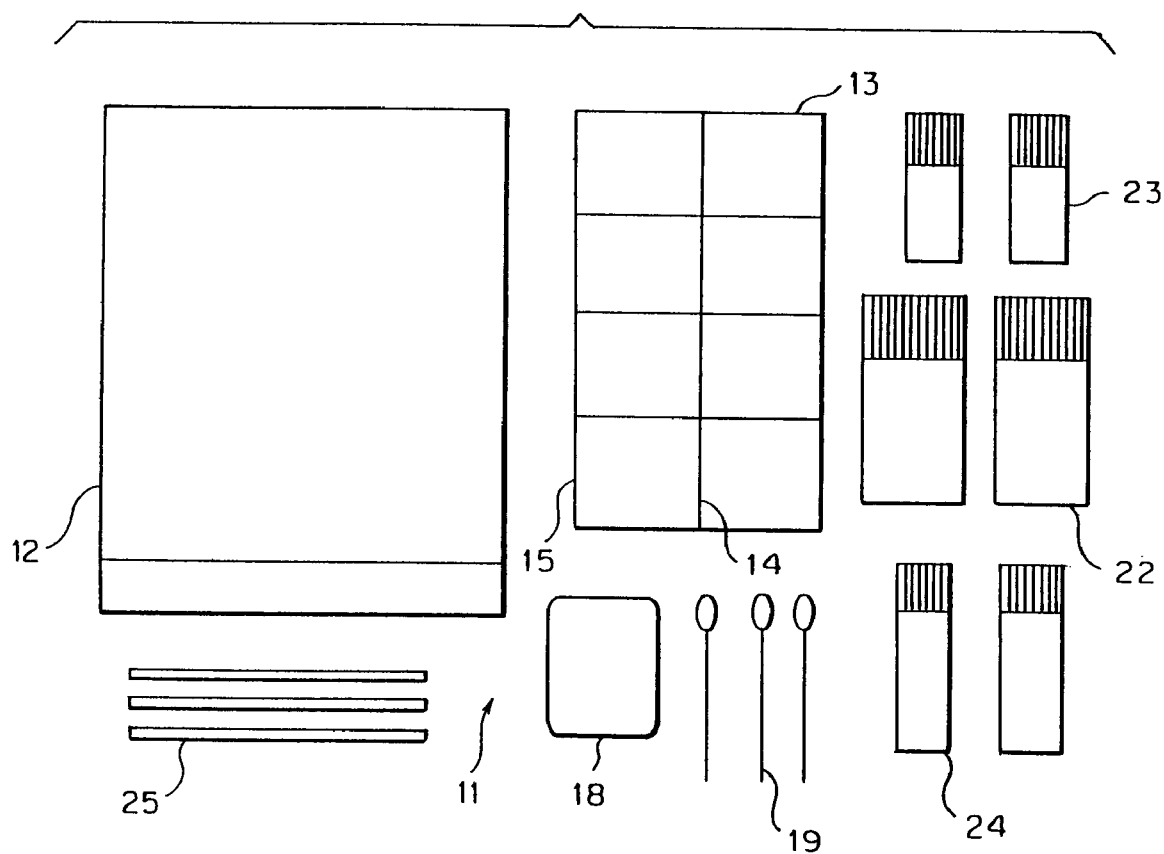
FIG.2
FIG.3
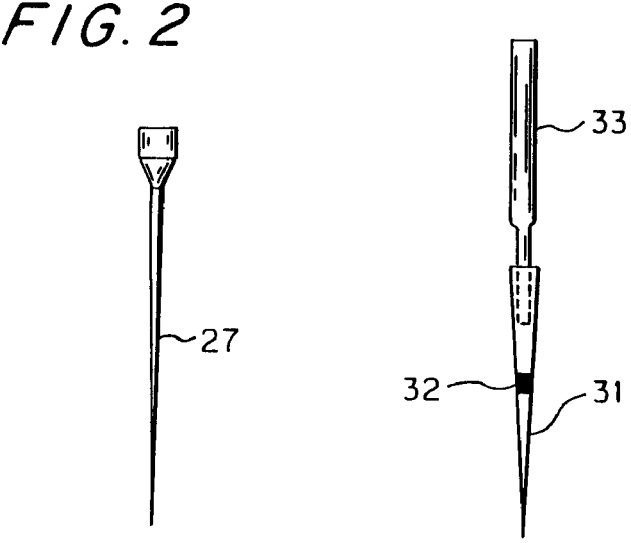

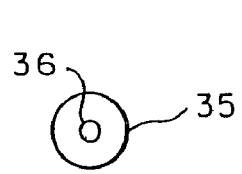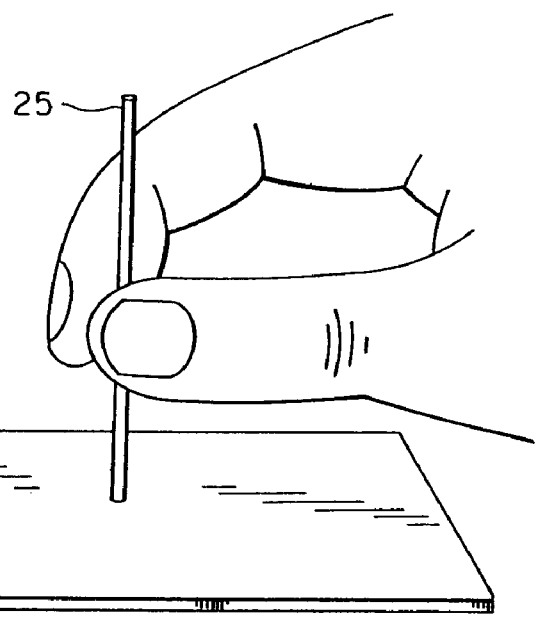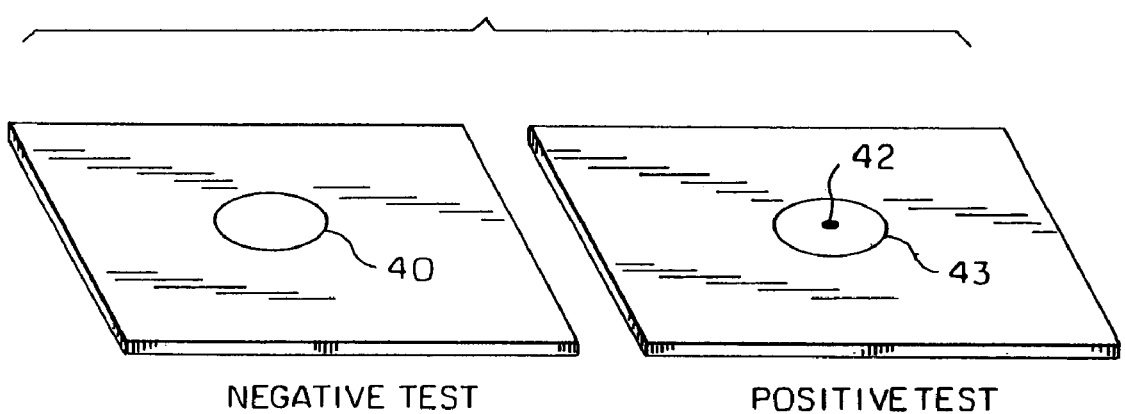

FIELD MICROSPOT TEST METHOD FOR ON-SITE CHEMICAL TESTING

This is a Continuation-In-Part of U.S. application Ser. No. 08/763,181, filed Dec. 11, 1996 now U.S. Pat. No. 5,935,862.

GOVERNMENT INTEREST

The invention described herein may be manufactured, licensed, and used by or for the U.S. Government.

BACKGROUND OF THE INVENTION

1. Field of the Invention

This invention relates to a field test kit and method of on-site testing for the presence of contaminants and chemicals, and more particularly to a micro spot method for detecting the presence of a variety of chemicals and environmental contaminants.

2. Description of the Prior Art

In view of biological hazards associated with toxic chemicals and environmental contaminants, regulations have been established by legislatures and environmental agencies to monitor a wide variety of chemicals and their byproducts. As a result, it is often necessary to conduct on-site inspections and analyses of various chemical spills, dump sites, and manufacturing facilities to detect environmental contaminants, hazardous conditions and to assure compliance with environmental regulations.

Advantages of on-site inspection and analysis of chemical sites include resolving ambiguities during the inspection, reducing the potential for contamination and cross-contamination of samples during travel to off-site testing laboratories, and providing a convenient method of performing a large number of preliminary tests to detect and screen for chemical contaminants. On-site inspection also provides a rapid indication of those samples which may possibly contain compounds that must be identified using more sophisticated laboratory analytical techniques. On-site testing also allows the level of concentration and spread of contamination from chemical spills to be readily surmised.

Reagent-based chemical detection and chromatographic methodologies are attractive for on-site testing and screening because many tests can be run in a short period of time and they are capable of providing visual presumptive evidence of the presence of a chemical substance in a sample. One methodology comprises classical spot tests that are normally carried out in depressions or wells of a porcelain spot plate. Conventionally, small amounts of a solution, which may contain chemical contaminants, are placed in the wells of the spot plate. Small quantities of different reagents are then added to the solution samples and a positive test is normally signified by a color change in the well of the spot plate. An advantage with these tests is that a number of tests can be carried out on a single plate. For example, as many as 12 different spot tests can be carried out on a small 3.5×4.5 inch spot plate. Another advantage is that it is possible to rapidly screen a large number of samples during a short period of time. However, as the concentration of the chemical substances become more dilute, it becomes more difficult to reliably detect the presence of the chemical substances. In most cases, the lower limit of detection is in the 1–100 microgram range.

Another methodology for screening samples and detecting target analytes in samples is use of thin layer chromatography (or TLC), which conventionally utilizes a plate having a surface layer formed of a sorbent material or gel. In order to separate the components of the analyte obtained from a sample, a drop of solution is carefully applied above the bottom edge of a thin layer chromatography plate. Solutions suspected of containing target analytes are preferably deposited onto the surface of a TLC plate in the form of a drop to avoid a streaking pattern that would result if the device for applying the drop actually contacts the surface of the plate while a sample solution is being deposited. After the solvent evaporates, the residue on the plate is eluted with another solvent or solvent mixture (also known as the eluant) thereby causing the chemical components of the sample to migrate towards the top or opposite edge of the plate. When the proper conditions and eluant are chosen, each analyte migrates across the plate at a rate that is different from the other analytes. The elution step results in the different analytes separating from each other and settling at different regions and as diffuse spots along the path of migration. After the elution step, the plates are allowed to dry and then they are sprayed with a solution of visualization reagent (detector reagent). A persistent concern with thin layer chromatography is that the elution step of waiting for the solvent to completely wet the plate and for the analytes to migrate and separate is relatively time-consuming. In many instances, proper completion of the elution phase may exceed an hour and warrant involved techniques and quality control steps to assure adequate separation of the different analytes. Another concern involves situations where the analytes are present in such low concentrations that the detection signals obtained in the tests are weak and can possibly be misread. In summary, with thin layer chromatography the analytes in the sample migrate and separate into localized regions, as opposed to concentrated at spots or points.

SUMMARY OF THE INVENTION

The micro spot test system and methodology of the present invention relates to an apparatus and method for the on-site testing of analytes contained in a sample by dissolving the analytes in a solvent and utilizing capillary deposition techniques to concentrate the analytes on sorbent materials. Detection sensitivity and accuracy for a range of concentrations of analytes is provided by applying a solution containing the analytes to a sorbent layer by capillary deposition so that the analytes in the solution become concentrated at the particular spot or point of deposition on the sorbent layer. The solutions are deposited by placing small diameter tubes containing the analyte solution in contact with the surface of the sorbent material so that the solutions are drawn from the small diameter tubes by capillary action. A detector reagent is then utilized to detect the presence of the analytes that are concentrated at the spot where the small diameter tube contacts the sorbent layer.

A system for chromogenically detecting the presence of chemical analytes includes a means for obtaining a sample solution containing the analytes; a device for the capillary deposition of the sample solution; chromatographic sorbent materials; and chromogenic detector reagents. Storage devices may be provided for the samples and for sample solutions; capillary deposition devices; the chromatographic sorbent materials and the chromogenic detector reagents.

Accordingly, one object of the present invention is to provide a compact chemical screening apparatus which is of a self-contained, efficient design for rapid screening of solutions for the presence or absence of target analytes.

Another object of the present invention is to provide a chemical screening device which is relatively simple to use for sample solutions containing a wide range of analytes in a wide range of concentration levels.

These, together with still other objects of the invention, along with the various features which characterize the invention, are pointed out[]with particularity in the appended claims.

BRIEF DESCRIPTION OF THE INVENTION

Other objects and advantages of the invention will become apparent upon reading the following detailed description with reference to the attached drawings, wherein:

FIG. 1 is a plan view of a field test kit for performing on-site chemical analysis;

FIG. 2 is a plan view of a pipet with a micro-tip;

FIG. 3 is a plan view of removable micropipet tips;

FIG. 4 is a view of the end portion of a capillary tube;

FIG. 5 is a view generally showing the end portion of a capillary tube in contact with a sorbent layer; and FIG. 6 is a plan view of a sorbent layer depicting the results of a micro spot test.

DETAILED DESCRIPTION OF THE PREFERRED EMBODIMENT

The micro spot system and methodology of detecting the presence of target analytes in a sample comprises the application of a solution containing the analytes to a chromatographic sorbent material by capillary action and adding a sufficient amount of a chromogenic detector reagent to form a chromogenic indicator when a target analyte is present in the sample. Apparatus for accomplishing this is generally shown in FIG. 1. In FIG. 1, the apparatus or kit 11 includes a bag or container 12 for storing the components of the system; at least one thin layer chromatographic plate or TLC plate 13; collecting devices such as cloth wipes 18 or swabs 19 for wiping surfaces for chemical residues; solvent containers 22; containers 23 for receiving the swabs and solvent solutions; reagent containers 24; and small diameter capillary or microcapillary tubes 25. A system or kit 11 for on-site detection and screening of a broad array of both volatile and non-volatile chemicals generally contains a wide variety of chemical reagents preferably stored in dry condition and in an inert atmosphere in small 2 to 3 ml. sealed containers or bottles 24, as represented in FIG. 1. Solvents for the samples and the reagents are stored in separate bottles 22 and an appropriate solvent is added to dissolve a reagent in the bottle in which it had been stored or in a separate container shortly prior to use. To insure a long shelf-life stability, the solid state reagents are preferably stored in dry condition, in an atmosphere that is free of moisture, and in which air has been displaced by an inert gas such as nitrogen or argon.

For purposes of this application, the term sample is defined as a representative fraction of the material that is to be processed and tested to detect the presence of an analyte. The sample may be a solid, such as soil, a liquid, such as water taken from a lake, or a vapor, such as fumes obtained from a chemical plant. An analyte is a chemical substance present in the samples that are being tested or analyzed. A solution is a homogeneous liquid that contains dissolved chemical substances. The analyte is a solute, which is defined as a chemical substance or mixture of chemical substances that dissolves in a solvent or a mixture of solvents to form a solution. A sample solution is a homogeneous liquid that contains dissolved chemical substances (i.e., the analytes or solutes) and which is derived by washing, extracting, or eluting a sample with a solvent or mixture of solvents. For example, surface wipes 18 or swabs 19 of polyester or similar material are used to obtain a sample by wiping a suspected surface. A sample solution is obtained for analysis by washing, extracting or eluting the wipe in a container 23 with a suitable solvent such as acetone, dichloromethane, hexane, etc. Soil samples can be washed, extracted or eluted in separate containers to obtain sample solutions. Aqueous samples suspected of containing a target analyte can be extracted with an immiscible solvent which is capable of extracting the analytes believed to be therein. In addition, solid phase extraction (SPE) or solid phase microextraction (SPME) techniques can be used to extract analytes from water for analysis using the micro spot tests.

Once the solution or liquid extract has been formed, and where necessary the extract has been concentrated by evaporation, a tube with a small diameter bore or opening 25, such as a small diameter capillary or microcapillary tube is used to collect and dispense small amounts of the solution onto the surface of plate 13 by capillary action. Preferably, the plates 13 are thin layer chromatographic plates or TLC plates having a surface layer formed of a chromatographic sorbent material. A sorbent material is a material that has both absorption and adsorption characteristics. Absorption is defined as the penetration of liquids into the bulk of a porous material somewhat like a sponge soaking up water. Adsorption is a process whereby a chemical substance, an analyte, sticks, clings or adheres to the surface of a solid constituent, the adsorbent. In FIG. 1, the plates have been provided with scoring lines 14 to divide the plate 13 into a plurality of separate sections 15 that serve as different test sites. Generally, the amount of sample delivered to a test site on the chromatographic material from a microcapillary tube having a length of one and one quarter inches is on the order of from about 0.1 microliters (for an approximate 0.05 mm diameter microcapillary opening) to about 30 microliters (for an approximate 1.6 mm diameter microcapillary opening) of sample. In most instances sample size will be on the order of from about 0.5 microliters (for an approximate 0.1 mm diameter microcapillary opening) to about 5 microliters (for an approximate 0.4 mm diameter microcapillary opening) and preferably, the sample will be on the order of from about 1 microliter (for an estimated 0.2 mm diameter microcapillary opening) to about 3 microliters (for an estimated 0.25 mm diameter microcap opening). Microcapillary tubes having longer lengths can be used. If desired, the microcapillary tube 25 can be held with commercially available holders or forceps.

The term "microcapillary tube" includes any tube made from glass, plastic or other material having a small diameter opening that is capable of dispensing liquid from (or drawing liquid into) the opening by capillary action. Examples of small diameter capillary tubes are those marketed by Drummond and sold under the trademarked name of Microcaps. Another type of tube having a small diameter opening is a micropipet. A micropipet is a glass or plastic tube having a small diameter opening (or capillary opening) at one end and an enlarged opening at the other end of the micropipet, as generally shown by micropipet 27 in FIG. 2. Examples of micropipets are Micro-tip polyethylene pipets sold by Micro Mole Scientific. One benefit of a micropipet is that if the top of the bulb is cut off, as shown in FIG. 2, the larger end functions as a funnel for holding a larger volume of fluid sample than could normally be held or drawn into a capillary tube. Consequently, a larger volume of sample (such as 10 microliters or more) can be used to achieve a higher detection sensitivity with respect to the concentration of analyte that can be detected. Replaceable micropipet tips 31, as shown in FIG. 3, are examples of additional devices that have small diameter openings. A removable micropipet tip 31 would be placed on the end portion of another tube 33 or container so that the liquid in the tube or container would be withdrawn by capillary action when placed in contact with a chromatographic sorbent material. An additional deposition control could be achieved by use of an in-line filter element 32 in a microcapillary device. One example of a micropipet tip is available under the tradename of Plasti-brand autoclavable nonsealing filter tips and another example of a micropipet tip without a filter is Catalog No. 71-6311-10 from PGC Scientific, Gaithersburg, Md. An example of a micropipet tip with a filter is Catalog No. 71-6311-16 from PGC Scientific, Gaithersburg, Md. While microcapillary tubes, micropipets and micropipet tips have been distributed for use with bulbs or other devices for forcing liquid out of the tubes, use of such pressure devices for forcing liquid from microcapillary tubes is contrary to the methodology of the present invention where the solution containing the analyte is deposited by capillary action. Further, while some methodology for applying a sample to a TLC plate with a microcapillary tube includes moving the tip of the microcapillary tube as the sample is being applied, use of such methodology that includes moving the tip of the microcapillary tube is contrary to the methodology of the present invention where all of the analyte contained in the sample solution must be adsorbed in the smallest volume of sorbent.

To avoid breaking extremely thin microcapillary tubes, micropipets and micropipet tips during use as the ends portions of these devices contact sorbent surfaces, it is possible to use various holding devices such as forceps and small clamps. While microcapillary tubes have been found acceptable for most applications, where conditions or technique warrant, the end portions of the tubes can be formed with thickened wall portions as shown in FIG. 4, where the thickness of the wall portions 35 are at least equal to the diameter of the opening 36 of the tube 25. Increasing the wall thickness to at least twice the diameter of the opening not only strengthens the end portion of the tubes for adverse use conditions, but also provides a larger contact surface area relative to the size of the opening and thereby promotes higher circumferential contact and seal of the microcapillary tubes with the sorbent material.

In general, the concentration of analyte in solution that is capable of being detected using a microcapillary tube to apply the solution containing the analyte to a thin layer chromatography plate (or TLC plate) in a micro-spot test is inversely related to the total volume of solution applied to the plate. For example, analytes present in solutions at low concentration levels can be detected by increasing the total volume of solution applied by capillary action to a TLC plate in the micro spot test. When using a microcapillary tube such as a micropipet to apply a relatively large volume of solution to a TLC plate, the sample solution being drawn from the tip of the micropipet should initially come in contact only with the area directly beneath the opening of the micropipet that contacts the TLC plate. One way for this condition to be met is that the solution can be added to the large end of the micropipet tube in small aliquots, so that the solution wets the TLC plate by capillary action. Another way for this condition to be met is that when a large volume of solution is added in a single aliquot to the micropipet, sufficient pressure should be exerted so that the micropipet tip completely contacts the TLC plate. When this occurs, the solution will wet the plate by capillary action. To promote well-defined small spots, the liquid solution should not be allowed to leak or flow from the juncture of the micropipet tip with the surface of the chromatographic sorbent layer of the TLC plate. A further methodology is to use a micropipet tip that contains a filter or other device within the tip that slows the flow of solution to ensure that the solution wets the TLC plate by capillary action when the solution is applied to the TLC plate by placing the tip in contact with the sorbent layer of the TLC plate.

Preferably, the sorbent layer should be capable of acting both as an adsorbent and as an absorbent. It is believed that when the sample solution, which contains an analyte (i.e., the solute) dissolved in a solvent, is applied to the sorbent by capillary action using a microcapillary device, the solute separates from the solution because it adheres or clings to the walls of the pores in a small volume of the sorbent immediately surrounding the point of application of the sample solution due to adsorption, while the solvent, a fluid which consequently has been freed from the solute, fills the voids in the pores of the sorbent due to absorption. This phenomenon results in the analyte concentrating within the sorbent layer and being localized in a small volume of the sorbent or "spot", while the solvent freely wets a substantial volume of sorbent. Since the volume of sorbent in which the solute is adsorbed is a small fraction of the volume in which the solvent is absorbed, the analyte becomes highly concentrated and consequently, high sensitivity of detection is made possible in the micro spot tests. When the analyte is present in very low concentration levels, application of the sample solution to the sorbent layer will result in the analyte concentrating in a very small volume of sorbent, and hence, will produce only a very small spot. Whereas, if the analyte is present in a somewhat higher concentration level, application of the sample solution to the sorbent layer will result in the analyte concentrating in a somewhat larger volume of sorbent, and hence, will produce a somewhat larger spot. FIG. 5 depicts a view where the end portion of a microcapillary tube has been placed in sufficient contact with a sorbent layer so that as the solution containing the analyte leaves the opening in the end portion of the tube, the analyte is adsorbed in a small localized region or spot about the point where the tip or end of the microcapillary tube contacts the sorbent layer, while the solvent spreads throughout the porous medium as it wets and is absorbed into the sorbent layer.

The chromatographic sorbent material is preferably a thin-layer chromatography (or TLC) plate. TLC plates are commonly found containing a silica gel or alumina coating. One example is MK6F Silica Gel 60A TLC plates, Catalog No.4861-110 from Whatman, Inc., Clifton N.J. 07014, which contains a 250 micron thick layer on a 1 by 3 inch glass microscope slide is a preferred solid support for the micro spot tests. These plates are relatively easy to handle and they contain a solid substance that fluoresces brightly when illuminated with short wavelength UV light. Therefore it is possible to detect substances that absorb UV light by "fluorescence quenching", as well as by other detection and visualization methods. A non-limiting list of suitable TLC strips which can be used in carrying out the invention include Diamomd MK6F Silica Gel 60A TLC plates, Catalog No. 4500-100 from Whatman, Inc., Clifton N.J. 07014, which contains a 250 micron thick layer on a 1 by 3 inch glass microscope slide; Silica Gel HL, 250 micron thick layer, Cat. No. 46931, Analtech, Newark, DE 19714; Silica Gel HLF, 250 micron layer, Cat. No. 47931, Analtech, Newark, DE 19714; Ammonium Sulfate (5%) Modified Silica Gel H, 250 micron layer, Self Charring Plates, Cat. No. 74031 (without indicator) and Cat. No. 75031 (with fluorescent indicator); Silica Gel F-254 TLC media, plastic backed, layer thickness 0.25 mm, Cat # 5775 from E. M. Laboratories, Elmsford, N.Y. 10523; Silica Gel F-254 TLC media, aluminum backed, layer thickness 0.2 mm, Cat # 5539 from Alltech Associates, Deerfield, Ill. 60115; Silica Gel TLC media, plastic backed, layer thickness 100 microns, Product Number 13179, Cat. # 4G 6801, Eastman Kodak Co., Rochester, N.Y. 14650; $C_{18}$/Silica Gel, 250 micron thick layer, Cat. No. 17021, Analtech, Newark, Del. 19714; $NH_2$/Silica Gel, 250 micron thick layer, Cat. No. 18021, Analtech, Newark, Del. 19714; CN/Silica Gel, 250 micro thick layer, Cat. No. 19021, Analtech, Newark, Del. 19714; Nano-SIL G High Performance Thin-Layer Chromatography (HPLTC) Plates, Catalog 81841, Alltech, Inc., Deerfield, Ill. 60015; Nano-SIL-NH2/UV (Amino). Catalog No. 8100026, Alltech, Inc., Deerfield, Ill. 60015; Nano-SIL-CN/UV (Cyano) Catalog No. 8110022, Alltech, Inc., Deerfield, Ill. 60015; Reversed Phase Sil Gel 60, RP-2 (Dimethyl bonded) Cat. No. 5746, RP-8 (Octyl bonded) Cat. No. 15388-7, RP-18 (Octadecyl bonded) Cat. No. 15389-7, Alltech Inc., Deerfield, Ill. 60015; "hybrid plates" (one plate designed for both reverse-phase and normal phase TLC), Catalog Number 818144, Alltech, Inc., Deerfield, Ill. 60015; Avicel Microcrystalline Cellulose Uniplates, 250 micron thick layer, Cat. No. 05061 (without indicator) and Cat. No. 06061 (with fluorescent indicator), Analtech, Newark, Del. 19714; SILCEL-Mix 25 UV254, Catalog No. 810043, Alltech, Inc., Deerfield, Ill. 60015; ALOX-100 UV254, Catalog No. 807033, Alltech, Inc., Deerfield, Ill. 60015; GUR N-25 UV254, Catalog No. 810073, Alltech, Inc., Deerfield, Ill. 60015; Nano-SIL C18-100 UV254, Catalog No. 811062, Alltech, Inc., Deerfield, Ill. 60015; SIL N-HR/UV254, Catalog No. 804023, Alltech, Inc., Deerfield, Ill. 60015; CEL 300 AC-30%, Catalog No. 801043, Alltech, Inc., Deerfield, Ill. 60015; CEL 300 DEAE, Catalog No. 801073, Alltech, Inc., Deerfield, Ill. 60015; Polyamide 6 UV254, Catalog No. 803023, Alltech, Inc., Deerfield, Ill. 60015; ALOX N/UV254, Catalog No. 802021, Alltech, Inc., Deerfield, Ill. 60015; Instant Thin Layer Chromatography Polysilicic Acid Gel Impregnated Glass Fiber Sheets with Fluorescent Indicator, Product Number 51435, Gelman Instruments, Ann Arbor, Mich. 48106; Instant Thin Layer Chromatography Sheets, Type SG, Product Number, 61886, Gelman Instrument Co., Ann Arbor, Mich. 48106; TLC Plates, Silica Gel 60 F-254, aluminum backed, layer thickness 0.2 mm, Product # 37360, Catalog # Z19,329-1, Aldrich Chemical Co., Milwaukee, Wis. 53233; Silica Gel IB Flexible (plastic backed) Sheets for Thin Layer Chromatography, layer thickness 250 microns, Product Number 4462-02, J. T. Baker, Inc., Phillipsburg, N.J. 08865; Aluminum Oxide IB Flexible (plastic backed) Sheets for Thin Layer Chromatography, layer thickness 200 microns, Product Number 4466-00, J. T. Baker, Inc., Phillipsburg, N.J. 08865; Reversed Phase (hydrocarbon impregnated) HPTLC Uniplates, 150 micron thick layer, Cat No. 54377 (without indicator) and Cat. No. 55377 (with fluorescent indicator), Analtech, Newark, Del. 19714; MKC18F Reversed Phase TLC plates, glass backed (1"×3" plates), layer thickness 200 microns, Cat. # 4803-110 from Whatman, Inc., Clifton, N.J. 07014; H-RP2F (ethyl bonded silica gel) Reversed Phase TLC plates, layer thickness 50 microns, Cat. No. 08527, Analtech, Newark, Del. 19714; Polyram Ionex 25 SA-NA Ion Exchange Resin and Silica Gel Mixed Layer on Plastic, Catalog Number M806013, Bodman Chemical Co., Aston, Pa. 19014; Polygram Ionex 25 SB-AC Ion Exchange Resin and Silica Gel Mixed Layer on Plastic, Catalog Number 806023, Bodman Chemical Co., Aston, Pa. 19014; and 2000 micron thickness Silica Gel G Preparative Uniplates, Catalog Number 01055, Analtech, Inc., Newark, Del. 19714. The composition of adsorbent coatings contained on the listed TLC plates include silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents.

If the thin-layer chromatography (or TLC) sheets or plates are those which are commercially available, they can be further scored into small sample areas within the sheet, i.e. ½ inch×½ inch or a similar size. The scoring of the plate reduces the likelihood that the liquid detector reagent applied in one spot test will creep into the sections reserved for other spot tests. Alternatively, the method can be carried out using TLC sheets that are specifically made to carry out the micro spot tests of the present invention.

After the sample solution is deposited on a TLC plate, a short period of time, generally on the order of about one minute, is allowed to elapse during which the solvent evaporates. Then, a sufficient amount of a detector reagent is added to the location on the TLC plate where the solution containing the analyte was deposited. It is to be understood that the solution containing the analyte can be deposited on a plurality of test sites on the TLC plates and different detector reagents can be used to test for the presence of target analytes or functional groups. Alternately, different sample solutions can be applied each to a different spot on a single TLC plate, and one detector reagent can be added to all of the analyte spots on the plate.

Examples of chromogenic detector reagents include bromcresol green; 7,7,8,8-tetracyanoquinodimethane (TCNQ); gold chloride (without NaOH); gold chloride/NaOH solution (i.e., the slash between the reagents means "followed by" and it is applicable to all of the reagent combinations); 4-(4'-nitrobenzyl)pyridine/NaOH; cholinesterase/indoxyl acetate; sodium pyrophosphate peroxide/aromatic amine; potassium bismuth iodide; 1,3-diisonitrosoacetone guanidinium salt; bis(diethylamino)benzophenone oxime; bis (diethylamino)benzophenone; bis(dimethylamino) thiobenzophenone; phenylazoformic acid 2-diphenylhydrazide; diphenylcarbazone; diphenylthiocarbazone; mercuric salt; diethyldithiocarbamic acid silver salt; 2,2'-dithiobis(5-nitropyridine); 5,5-dithiobis(2-nitrobenzoic acid) i.e., Ellman's Reagent; molybdenum oxide in sulfuric acid; ammonium molybdate; iodine/starch; and sulfuric acid (4M). Below is a non-limiting partial list of other detector reagents that can be used in the methodology described herein. Other detector reagents are contained in references 1–38 which are incorporated herein by reference.

TABLE 1

Partial List of Detector Reagents for Microspot Tests

| Detector Reagent | Target Analytes |
|---|---|
| alizarin | cations |
| aluminum chloride | flavonoids |

TABLE 1-continued

Partial List of Detector Reagents for Microspot Tests

| Reagent | Analyte |
|---|---|
| 4-aminoantipyrine/potassium hexacyanoferrate | phenols |
| o-aminodiphenyl/phosphoric acid | sugars |
| 4-aminohippuric acid | reducing sugars |
| o-aminophenol/phosphoric acid | sugars |
| ammonia | tetracyclines |
| ammoniun cerium(IV)nitrate | polyalcohols |
| ammonium cerium(IV)nitrate/nitric acid | alpha-hydroxy acids, alpha-keto acids, mercaptans |
| ammonium cerium(IV)sulfate | alkaloids |
| ammonium iron(III)sulfate | flavonoids |
| ammonium iron(III)sulfate | alkaloids |
| ammonium molybdate/crystal violet | phosphoric acid |
| ammonium molybdate/tin(II)chloride | phosphoric acids |
| ammonium thiocyanate/iron(II)sulfate | peroxides |
| aniline/diphenylamine/phosphoric acid | reducing sugars |
| aniline/phosphoric acid | sugars |
| aniline phthalate | reducing sugars, anions of halogen oxyacids |
| anisaldehyde/sulfuric acid | sugars, steroids, terpenes |
| p-anisaldehyde | reducing sugars |
| p-anisidine phthalate | reducing sugars |
| anthrone | ketoses |
| antimony(III)chloride | flavonoids |
| antimony(III)chloride | vitamin A and D, carotenoids, steroids, sapogenins, steroid glycosides, terpenes, sapogenins resins, steroid |
| aurin tricarboxylic acid (aluminon) | aluminum ions, chromium ions, lithium ions |
| 2,2'-bipyridine/iron(II)chloride | phenols, vitamin E, reducing compounds |
| bismuth chloride | sterols |
| boric acid/citric acid | quinolines |
| bromine/fluorescein/silver nitrate | insecticides |
| bromocresol green (or bromcresol green) | organic and inorganic acids, |
| bromocresol green/bromophenol blue/ potassium permanganate | organic acids |
| bromocresol purple | dicarboxylic acids, halogen ions |
| bromophenol blue/methyl red | phenols |
| bromosuccinimide/fluorescein | lipids, sulfur compounds |
| cacotheline | vitamin C |
| carbazole/sulfuric acid | sugars |
| carmine | polysaccharides |
| cerium(IV)sulfate | organic and inorganic iodine compounds |
| cerium(IV)sulfate/nitric acid | polyphenylenes |
| cerium(IV)sulfate/sulfuric acid | alkaloids, iodo-organic compounds |
| chloramine-T | caffeine |
| chloramine-T/trichloroacetic acid | digitalis glycosides |
| 1-chloro-2,4-dinitrobenzene | nicotinic acid, nicotinamide, pyridoxol |
| chlorosulfonic acid/glacial acetic acid | triterpenes, sterols, steroids |
| chromosulfuric acid | organic compounds |
| chromotropic acid | methylenedioxyphenyl-type compounds nicotine, hydrastine, sesamine |
| cinnamaldehyde/acetic anhydride/sulfuric acid | steroid sapogenins |
| cinnamaldehyde/hydrochloric acid | indole derivatives |
| cobalt(II)chloride | organic phosphate esters |
| cobalt(II)/lead nitrite | ammonium ions, potassium ions |
| cobalt(II)nitrate/ammonia | barbiturates |
| cobalt(II)nitrate/lithium hydroxide | barbiturates |
| cobalt(II)thiocyanate | alkaloids, amines |
| copper acetate/potassium hexacyanoferrate(II) | higher fatty acids |
| copper acetate/rubeanic acid | higher fatty acids |
| copper chloride | oximes |
| copper sulfate/quinine/pyridine | barbiturates, thiobarbiturates |
| copper(II)sulfate/sodium citrate | flavonoids, coumarins with o-dihydroxy groups |
| alpha-cyclodextrin | straight-chain lipids |
| cysteine/sulfuric acid | desoxyribonucleosides |
| 3,5-diaminobenzoic acid/phosphoric acid | 2-deoxy-sugars |
| o-dianisidine | aldehydes, ketones |
| 2,6-dibromoquinone chlorimide | phenols |
| 2',7'-dichlorofluorescein (fluorogenic indicator) | saturated and unsaturated lipids |
| 2',7'-dichlorofluorescein/aluminum chloride/iron(III)chloride | free fatty acids |
| 2,6-dichlorophenolindophenol/silver nitrate | alkali chlorides |
| 2,6-dichlorophenolindophenol sodium salt | organic acids, keto acids, vitamin C |
| 2,6-dichloroquinone chlorimide | antioxidants, adrenaline and derivatives, cyanamide and derivatives |
| dicobalt octacarbonyl | acetylene compounds |
| diethylamine/copper(II)sulfate | thiobarbiturates |
| diethyl malonate | 3,5-dinitrobenzoic acid esters |
| dimedone/phosphoric acid | keto-sugars |
| 4-dimethylaminobenzaldehyde/acetic acid/phosphoric acid | proazulenes, azulenes |
| 4-dimethylaminobenzaldehyde/acetylacetone | amino-sugars |
| 4-dimethylaminobenzyaldehyde/hydrochloric acid | amines |
| 4-dimethylaminobenzaldehyde/sulfuric acid | ergot alkaloids |
| dimethylaminobenzylidenerhodanine | silver ions, copper ions, mercury ions |
| 4-dimethylaminocinnamaldehyde | indoles |
| dimethyl-p-phenylenediamine dihydrochloride | peroxides |
| dimethyl-p-phenylenediamine dihydrochloride/trichloroacetic acid | methyl-sugars |
| 1,3-dinitrobenzene | 17-ketosteroids |
| 3,5-dinitrobenzoic acid | cardiac glycosides |
| 3,5-dinitrobenzoic acid | reducing sugars |
| 2,4-dinitrofluorobenzene | amino acids |
| 2,4-dinitrophenylhydrazine | free aldehyde groups, free keto groups, ketoses |
| 3,5-dinitrosalicylic acid | reducing sugars |
| diphenylamine | glycolipids |
| diphenylamine/palladium(II)chloride | nitrosamines |
| diphenylamine/zinc chloride | chlorinated insecticides |
| diphenylboric acid-beta-aminoethyl ester | alpha and gamma-pyrones |
| diphenylcarbazide | silver ions, lead ions, mercury ions, copper ions, tin ions, zinc ions, calcium ions |
| diphenylcarbazone | addition compounds of unsaturated fatty acids |
| diphenylcarbazone | cations |
| diphenylpicrylhydrazyl | essential oils |
| 2,5-diphenyl-3-(4-styrylphenyl)-tetrazolium chloride | reducing steroids, corticosteroids |
| dipicrylamine | choline, vitamin B1 |
| dithizone | ions of heavy metals |
| 4,4'-dithiodianils | thiols |
| Dragendorff reagent | polyethylene glycols, polyethylene glycol ethers, quaternary bases, alkaloids, nitrogen-containing compounds |
| ethylenediamine | catechol amines |
| ethylenediamine/potassium hexacyanoferrate | adrenaline, noradrenaline, acetyl derivatives |
| Fast blue salt B | phenols, coupling amines |
| fluorescein | lipids |

TABLE 1-continued

Partial List of Detector Reagents for Microspot Tests

| Reagent | Detects |
|---|---|
| fluorescein/ammonia | purines, pyrimidines, barbiturates |
| fluorescein/bromine | unsaturated compounds |
| fluorescein/hydrogen peroxide | hypnotics containing bromine |
| fluorescein/rhodamine-B/sodium carbonate | chlorinated hydrocarbons, heterocyclic compounds |
| formaldehyde/hydrochloric acid | indoles, indole derivatives |
| formaldehyde/phosphoric acid | steroid alkaloids, steroid sapogenins, phenothiazine derivatives |
| formaldehyde/sulfuric acid | aromatic compounds |
| furfural/sulfuric acid | carbamate esters |
| glucose/aniline | acids |
| glucose/phosphoric acid | aromatic amines |
| glyoxalbis(2-hydroxyanil) | cations |
| hydrazine sulfate | piperonal, vanillin, ethyl vanillin |
| hydrochloric acid | glycals |
| hydrogen peroxide | aromatic acids |
| 4-hydroxybenzaldehyde/sulfuric acid | sapogenins, corticosteroids |
| hydroxylamine/iron(III)chloride | lactones, esters, amides, anhydrides of carboxylic acids |
| 8-hydroxyquinoline | barium ions, strontium ions, calcium ions |
| 8-hydroxyquinoline/hypobromite | guanidine derivatives |
| indandione | carotenoid aldehydes |
| iodine | general detection reagent |
| iodine/potassium iodide | alkaloids |
| iodine/potassium iodide | organic compounds |
| iodine/sulfanilic acid/N-(1-naphthyl)ethylene diamine | hydroxylamines |
| iodine/sulfuric acid | organic compounds containing nitrogen, polyethylene glycols, polyethylene glycol derivatives |
| iron(III)chloride | phenols, hydroxamic acids |
| iron(III)chloride/iodine | xanthine derivatives |
| iron(III)chloride/potassium hexacyanoferrate(III)/arsenite | thyroid hormones, iodine containing compounds |
| iron(III)chloride/sulfosalicylic acid | thiophosphate esters |
| iron(III)chloride/sulfuric acid | indol derivatives |
| iron(II)thiocyanate | peroxides |
| isatin/sulfuric acid | thiophene derivatives |
| isatin/zinc acetate | amino acids |
| isonicotinic acid hydrazide | ketosteroids |
| lead acetate (basic) | flavonoids |
| lead(IV)acetate | 1,2-diol groups |
| lead(IV)acetate/rosaniline | 1,2-diol groups |
| magnesium acetate | anthraquinone glycosides |
| mercury chloride/diphenylcarbazone | barbiturates |
| mercury(II)chloride/potassium iodide | steroid alkaloids |
| mercury(I)nitrate | barbiturates |
| methylene blue | sulfate esters of steroids |
| methylunmbelliferone (fluorogenic detector reagent) | heterocyclic compounds containing nitrogen |
| methyl yellow | chlorinated insecticides |
| molybdatophosphoric acid | reducing compounds, lipids, sterols, steroids |
| morin | aluminum ions |
| 1,3-naphthalenediol/phosphoric acid | sugars |
| 1,3-naphthalenediol/sulfuric acid | sugars |
| 1,3-naphthalenediol/trichloroacetic acid | sugars, uronic acids |
| 1-naphthol/hypobromite | quanidine derivatives |
| naphthoquinone-sulfonic acid sodium salt | amino acids, aromatic amines |
| 1-naphthylamine | 3,5-dinitrobenzoic acid esters, dinitrobenzamides |
| ninhydrin | amino acids, amines, amino-sugars, |
| ninhydrin/cadmium acetate | amines, amino acids |
| ninhydrin/copper(II)nitrate | amino acids |
| ninhydrin/tin(II)chloride | amines |
| 2-nitroso-1-naphthol-4-sulfonic acid | iron ions |
| palladium(II)chloride | thiophosphate esters, organophosphorus insecticides |
| phenol/sulfuric acid | sugars |
| m-phenylenediamine | reducing sugars |
| p-phenylenediamine/phthalic acid | conjugated 3-ketosteroids |
| o-phenylenediamine/sulfuric acid | dehydroascorbic acid |
| o-phenylenediamine/trichloroacetic acid | alpha-keto acids |
| phenylfluorone | germanium |
| phenylhydrazine | dehydroascorbic acid |
| phosphoric acid | sterols, steroids |
| phosphoric acid/bromine | digitalis glycosides |
| potassium hexacyanoferrate(II) | iron(III) ions |
| potassium hexacyanoferrate(III) | adrenaline and derivatives |
| potassium hexacyanoferrrate(III) | vitamin B1 |
| potassium hexacyanoferrate(III)/iron(III)chloride | reducing compounds, phenols, amines, thiosulfates, isothiocyanates |
| potassium hexacyanoferrate(III)/phosphate buffer | adrenaline |
| potassium hexacyanoferrate(III)/potasssium hexacyanoferrate(II) | morphine |
| methanolic potassium hydroxide | coumarins, anthraquinone glycosides |
| potassium iodide/hydrogen sulfide | heavy metal ions |
| potassium iodide/starch | peroxides |
| potassium iodine plateate | alkaloids, other organic compounds containing nitrogen, ketosteroids |
| potassium permanganate (alkaline) | reducing compounds, sugars, aromatic polycarboxylic acids, polyalcohols |
| potassium permanganate (neutral) | easily oxidizable compounds |
| quinalizarin | cations |
| p-quinone | ethanolamine |
| resorcinol/zinc chloride/sulfuric acid | phthalate esters |
| resorcyl aldehyde/sulfuric acid | 16-dehydrosteroids |
| rhodamine 6G | lipids |
| rhodanine | carotenoid aldehydes |
| rhodizonic acid sodium salt | barium ions, strontium ions |
| rubeanic acid | lead ions, cobalt ions, copper ions manganese ions, nickel ions, mercury ions, bismuth ions |
| silver nitrate | phenols |
| silver nitrate/ammonia | sugars, sugar alcohols |
| silver nitrate/ammonia | reducing substances |
| silver nitrate/ammonia/fluorescein | halogen ions |
| silver nitrate/ammonia/sodium chloride | thioacids |
| silver nitrate/ammonia/sodium methodoxide | sugars |
| silver nitrate/bromophenol blue | purines |
| silver nitrate/fluorescein | alkylsulfonic acids arylsulfonic acids |
| silver nitrate/formaldehyde | chlorinated insecticides, dieldrin, aldrin, lindane |
| silver nitrate/potassium dichromate | barbiturates |
| silver nitrate/potassium permanganate | reducing compounds |
| silver nitrate/sodium dichromate | purines |
| silver nitrate/sodium hydroxide | sugars, polyalcohols |

TABLE 1-continued

Partial List of Detector Reagents for Microspot Tests

| | |
|---|---|
| sodium meta-periodate | hydroxyamino acids serine, threonine |
| sodium meta-periodate/4-nitroaniline | deoxy-sugars |
| sodium nitrite/hydrochloric acid | indoles, thiazoles |
| sodium nitroprusside | compounds with sulfhydryl group |
| sodium nitroprusside/acetaldehyde | secondary aliphatic and alicyclic amines |
| sodium nitroprusside/ammonia | hemlock alkaloids |
| sodium nitroprusside/hydroxylamine | thiourea derivatives |
| sodium nitroprusside/potassium hexacyanoferrate(III) | aliphatic nitrogen compounds cyanamide, guanidine, urea, thiourea, thiourea derivatives, creatine, creatinine |
| sodium nitroprusside/potassium permanganate | sulfonamides |
| sodium nitroprusside/sodium hydroxide | methyl ketones activated methylene groups |
| sodium nitroprusside/sodium meta-periodate | deoxy-sugars |
| sodium pentacyanoamino ferrate(II) | urea, thiourea, guanidines |
| sodium sulfide (aqueous solution) | hydrogen sulfide group |
| sodium tetraphenylboron | alkaloids |
| sodium tetraphenylboron/rhodamine B | potassium ions |
| sodium thiosulfate/copper(II)acetate | antimony ions |
| starch | amylases |
| sulfanilic acid/1-naphthylamine | nitrosamines |
| sulfuric acid | general visualization |
| sulfuric acid/hypochlorite | digitalis glycosides reagent |
| tetracyanoethylene | aromatic hydrocarbons, phenols, heterocyclic compounds |
| tetranitrodiphenyl | cardiac glycosides |
| tetraphenyldiboroxide | flavones |
| tetrazolium blue | corticosteroids, reducing compounds |
| thiobarbituric acid | sorbic acid |
| thymol/sulfuric acid | sugars |
| thymol blue | dimethylamino acids |
| tin(II) chloride/hydrochloric acid/4-dimethylaminobenzaldehyde | aromatic compounds containing nitro groups |
| tin(II) chloride/potassium iodide | gold ions |
| tin(IV) chloride | triterpenes, sterols, steroids, phenols, polyphenols |
| titan yellow | cadmium ions |
| p-toluenesulfonic acid | steroids, flavonoids, catechins |
| o-tolidine (fluorogenic detector reagent) | chlorinated insecticides |
| toluidine blue | acidic polysaccharides |
| trichioroacetic acid | steroids, digitalis glycosides, Veratrum alkaloids, vitamin D |
| trifluoroacetic acid | steroids |
| N,2,6-trichloro-p-benzoquinoneimine | thiophosphate pesticides |
| 2,4,6-trinitrobenzoic acid | cardiac glycosides |
| 2,3,5-tripheyltetrazolium chloride | reducing sugars, corticosteroids, reducing compounds |
| tungstophosphoric acid | reducing compounds, lipids, sterols, steroids |
| urea/hydrochloric acid | sugars |
| vanillin/hydrochloric acid | catechins |
| vanillin/phosphoric acid | steroids |
| vanillin/potassium hydroxide | ornithine, lysine, proline, amines |
| vanillin/sulfuric acid | higher alcohols, phenols, steroids, essential oils |
| violuric acid | alkali and alkaline earth metal ions |
| xanthydrol | tryptophan, indole derivatives |
| zinc chloride | steroid sapogenins, steroids |
| zinc uranyl acetate | sodium ions |
| zirconyl chloride/alizarin/hydrochloric acid | fluorine ions |
| zirconyl chloride/citric acid | glycosides |

It is generally expected that one drop of a detector reagent(s) will be sufficient in order to produce a result. However, in tests where two detector reagents are added in sequence, the second detector reagent should be added about two minutes (or more) after the first reagent. In some tests heat can be used to accelerate the reaction of a detector reagent with the analyte. If the test is positive, in most cases a small spot within the reagent spot on the TLC sheet changes color, often instantaneously, but with low analyte levels it will generally require a longer period of 15–60 seconds. Since the level of analyte tends to be directly related to the size of the color change within the spot, some quantification of the analyte levels may be possible. With the micro spot test, positive tests were obtained where the amount of analyte in a solution applied to a TLC plate was as low as 10 ng (see examples 1–5 below). One analyte, EMPTA, was also detected at the 1 ng level (see example 3 below). It is also possible to detect an analyte where the detection signal produced with the disclosed methodologies is a change in the intensity of color rather than an actual color change. For example, strong bases can be detected in disclosed micro spot test of the present invention where Bromcresol Green is the detector reagent. The detection signal that was produced was a small dark blue spot within a light blue spot in the test with Bromcresol Green when the analyte was a strong base.

FIG. 6 is a plan view of a sorbent layer depicting how the results of a microspot test may appear after a detector reagent has been added to the surface of a sorbent layer. The two circular spots or regions 40 and 42 are generally representative of where the detector reagent solution has been added to a sorbent layer. The spot to the left 40 represents the results when a negative result is produced (no analyte is present) and the spot to the right 42 represents the results when a positive result is produced (an analyte is present, producing a chromogenic indication). The right spot is shown to contain a smaller spot or point 43 in the center of the detctor reagent spot to represent that the unknown has been localized about the point where the microcapillary tube contacts the sorbent material. While there may be some expansion of the spot relative to the size of the opening, such as would occur with a relatively high concentration of analyte or use of different solvents, the analyte generally remains concentrated at the identified spot of deposition.

It was found that high detection sensitivity is attained with the disclosed methodology where the analyte is dissolved in a solvent and then applied in small amounts to a thin-layer chromatography media by capillary action using a microcapillary tube. Thus, the test method of the present invention is referred to as micro spot tests due to the minute quantities of analyte that are capable of being detected. It is further believed that the increased sensitivity of the micro spot tests is due at least in part to the fact that the analyte remains concentrated and localized at the spot of deposition.

The micro spot test method is generally solvent dependent, with respect to both the solvents for the analyte and the detector reagent. In general, the solvent for target analytes should be selected so that the analytes are concentrated in a small spot when the solution containing the analytes is applied to a TLC plate with a microcapillary tube. The solvent for the detector reagent should be selected so that the spot containing the analytes is not enlarged too much or washed from the TLC plate when the detector reagent solution is applied. For example, the silica gel and aluminum oxide (alumina) sorbents in TLC plates are polar compositions. When a solution that contains an analyte is applied to a polar sorbent coating such as silica gel or alumina with a microcapillary tube, a smaller and more compact spot will tend to form if the solvent for dissolving the analyte is closer to the low polarity end of the polarity scale. The low polarity or less polar solvent can be a solvent selected from the group that includes acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane. In this example, the solvent for the detector reagent is preferably the least polar solvent in which the detector reagent has adequate solubility. The solvent for the detector reagent can be selected from the following list of solvents acetic acid, water, aqueous buffer solution with a pH in the range 2–12, dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane.

If the solvent in which the detector reagent is dissolved is too polar, then when the detector reagent solution is applied to the analyte spot on the TLC plate, the analyte spot may tend to become enlarged and the resulting analyte density in the spot may be decreased. Thus, for polar sorbent materials, where the solvent for the detector reagent solution is too polar, the detection sensitivity for the analyte of interest may be reduced.

For polar media such as ion-exchange TLC plates, in general, the solvent for the detector reagent should be an aqueous solution in which the predominant component is water.

For non-polar adsorbents such as reversed phase TLC plates, in general, the solvent or solvents included in a solvent mixture for dissolving the analytes as well as the detector reagent are preferably selected from solvents close to the high polarity end of the polarity scale. Solvents that can be selected for preparing a highly polar solvent mixture for use with reversed phase TLC plates include water, methanol, N,N-dimethylformamide, acetonitrile, acetic acid, acetone, pyridine, ethanol, dioxane, chloroform, isopropanol, ethyl acetate, tetrahydrofuran, and n-propanol.

It is also possible to conduct a micro spot test by first applying the detector reagent to the TLC plate and allowing the solvent for the detector reagent to evaporate. Then, the solution containing the analyte is applied to the sorbent media or TLC plate. If this procedure is used, a detector reagent should be selected that is insoluble (or has very low solubility) in the solvent that is used to dissolve the analyte. If the detector reagent has some solubility in the solvent for the analyte, in a positive test result, a ring of the indicator may form instead of a small spot. Consequently, the detection sensitivity for the analyte may be poorer. Attractive advantages of applying the detector reagent to a TLC plate prior to applying the solutions containing the analyte(s) include (a) the liquid detector reagent solutions do not need to be prepared just prior to the test, (b) the required detector reagents can be pre-deposited at different locations on the same TLC media prior to on-site testing, and (c) the actual on-site testing steps are reduced to the microcapillary deposition of solutions containing the analytes and visual observation of the results.

To insure a long shelf life-stability for pre-deposited reagents, the prepared plates are preferably stored in dry condition, in an atmosphere that is free of moisture, and in which air has been displaced by an inert gas such as nitrogen or argon.

Most of the analytes that are separated and then detected using thin layer chromatography (TLC) or paper chromatography (PC), including, but not limited to, those detected using either a chromogenic or fluorogenic visualization reagent (often referred to as TLC or PC spray reagent), should be capable of being detected with high detection sensitivity using the micro spot test methodology described herein.

An illustrative methodology of carrying out the methods of the present invention is provided below:

A sample suspected of containing the analyte methylphosphonic acid is prepared by forming an acetone eluate from a polyester wipe. A microcapillary tube is used to draw up about 1 microliter of a solution containing the analyte and the end of the capillary tube is touched to a piece of a chromatographic sorbent medium, such as a TLC plate or medium. The analyte solution wets the sorbent layer by capillary action. Afterward, the TLC medium was allowed to dry and a drop of Bromcresol Green reagent was added. This caused a small yellow spot to be produced within a background of a large dark blue spot. This indicates that the acid has been retained near the spotting point due to its strong interaction with the chromatographic sorbent material. Since the analyte collects in a small area near the spotting point as a result of capillary action and being adsorbed into the TLC media, it is possible to detect minute quantities of the analyte. When the technique is used of bringing a microcapillary tube into contact with the surface of a TLC media, the analyte solution will exit from the microcapillary tube by capillary action. If the microcapillary tube is not kept in contact with the surface of the chromatographic media, a droplet larger than the diameter of the microcapillary tube may form. When a droplet larger than the diameter of the microcapillary tube forms and then comes in contact with the thin layer chromatographic media, the solution will wet a larger area and the analyte will not be as concentrated in a compact spot. Consequently, the detection sensitivity of the test may be poorer.

While this micro spot methodology has particular application to the detection of chemical warfare agents and examples of such applicability are given to demonstrate such applicability, the methodology is likewise applicable for use in conjunction with or in place of other thin layer chromatographic tests for environmental pollutants, contaminants, and hazards. Table 2 contains a list of compounds that are representative of the Priority 1 Analytes that can be detected with the processes of the present invention. This list represents a number of analytes that might be expected to be found during an on-site chemical weapons verification inspection. It will be understood by those of ordinary skill in the art that those analytes not specifically mentioned but known are also included herein and that the analyses for these analytes would be handled by the same methodology as analytes that are listed.

TABLE 2

PRIORITY 1 ANALYTES

| COMPOUND | SYNONYM |
|---|---|
| ethyl N,N-dimethylphosphoramidocyanate | GA |
| Isopropyl methylphosphonofluoridate | GB |
| Pinacolyl methylphosphonofluoridate | GD |
| Cyclohexyl methylphosphonofluoridate | GF |
| O-ethyl S-(2-diisopropylamino)ethyl methylphosphonothiolate | VX |
| bis(2-chloroethyl)sulfide | HD |
| bis[2-(2-chloroethylthio)ethyl]ether | T |
| 2-chlorovinyldichloroarsine | L |
| Methylphosphonic difluoride | DF |
| ethyl 2-(diisopropylamino)ethyl methylphosphonite | QL |
| Isopropyl methylphosphonic acid | IMPA |
| Pinacolyl methylphosphonic acid | PMPA |
| Cyclohexyl methylphosphonic acid | CMPA |
| Methylphosphonofluoridic acid | MPFA |
| Methylphosphonic dichloride | DC |
| S-(2-diisopropylamino)ethyl methylphosphonothioic acid | EA 2192 |
| ethyl methylphosphonic acid | EMPA |
| O-ethyl methylphosphonothioic acid | EMPTA |
| 1,4-dithiane | DITHIANE |
| 2-chlorovinylarsenious oxide | L-OXIDE |
| Methylphosphonic acid | MPA |

According to another aspect of the invention, there is provided a method whereby a more specific indication of the analytes can be achieved by using two or more micro spot tests in combination. By using a series of spot tests, the user is able to accumulate evidence for or against the presence of a Priority 1 Analyte in the sample without actually identifying any of the specific chemical components of the sample. This is important because the acceptance of the on-site screening procedures by the chemical industry may ultimately depend on methodologies that minimize or eliminate the need for unnecessarily subjecting chemical samples to sophisticated, and potentially more intrusive, analytical methods.

If a sample unknown gives positive tests for one or more Priority 1 Analyte, TLCs could be used to determine if the suspect sample is a mixture, and to obtain $R_f$ value(s) of the suspect analyte(s). For example, the TLC can be used to show the relative positions (from which $R_f$ values are obtained) for spots resulting from, for example, phosphonic acids and dithiane. The data can be obtained using a procedure similar to that developed by Sass and Ludemann for the separation of phosphonic acids, see J. of Chromatography, 187, 447–452 (1980), the contents of which are incorporated herein by reference. It is also noteworthy to mention that the shape of a spot on the TLC media and the rate at which the spot becomes colored when contacted by the visualizing reagent may also help to indicate which analyte is present. For example, a characteristic of the EMPTA spot is that it produces spots that have a long tail. Another characteristic of the EMPTA spot is that it changes color, going rapidly from colorless to brown when the TLC media is exposed to iodine vapor. While the micro spot test data may not be sufficient to identify the components of the unknown sample (which nonetheless is a desirable feature for screening tests), it is clear that the methods of the present invention can provide a considerable amount of evidence for the presence (or absence) of Priority 1 Analytes in a suspect sample.

Table 3 contains data that exemplify how three of the micro spot tests can be used in combination to accumulate presumptive evidence for the presence of several different Priority 1 Analytes. The sample unknown for the micro spot tests is one that would contain one of the following Priority 1 Analytes: MPA, EMPA, IMPA, PMPA, EMPTA and dithiane. For example, the data in Table 3 indicates that the response patterns from the three different spot tests can be used to distinguish dithiane and EMPTA from each other, and from MPA and several alkyloxy methylphosphonic acids that are also Priority 1 Analytes. A positive test result with the Bromcresol Green Test indicates that an acidic analyte, which could be MPA, or alkyloxy methylphosphonic acid, is in the sample. If the positive test with Bromcresol Green is combined with positive tests with TCNQ (7,7,8,8-tetracyanoquinodimethane) and gold chloride/NaOH, the response pattern could indicate that EMPTA may be present, but not dithiane, MPA or the alkyloxy methylphosphonic acids. A positive test with Bromcresol Green in combination with negative tests with TCNQ and gold chloride/NaOH indicates that a sample might contain MPA or one or more alkyloxy methylphosphonic acids, but not EMPTA or dithiane. Negative tests with Bromcresol Green and TCNQ combined with a positive gold chloride/NaOH test indicate that the sample may contain dithiane, but none of the phosphorus acids. Detection specificity is further improved when two or more tests are used in combination because different tests for the same analyte have different interference profiles.

TABLE 3

Results of Micro Spot Tests for Some Priority 1 Analytes

| | Reagent(s) for Micro Spot Test | | |
|---|---|---|---|
| | Bromcresol Green | TCNQ | Gold Chloride/NaOH |
| Analyte | | | |
| MPA | + | − | − |
| EMPA | + | − | − |
| IMPA | + | − | − |
| PMPA | + | − | − |
| EMPTA | + | + | + |
| DITHIANE | − | − | + |

Without additional data from other tests, however, the three spot tests used to obtain the data for Table 3, will not indicate if the unknown is a single substance or a mixture, and they will not indicate which phosphorus-containing acids may be present in the sample. However other tests could be used to provide more definitive results.

The following non-limiting examples further serve to illustrate the invention.

EXAMPLE 1

Micro Spot Test for Methylphosphonic Acids Using Bromcresol Green

Detection Principle

A positive test is the appearance of a yellow spot in a larger blue spot. The control (analyte level=0) and negative tests are indicated by a blue spot that does not contain a yellow center. The color change that is observed in a positive test is due to the difference in the pH of the analyte (pH 3 and above) and the solid support (pH>5). At pH 3.8 and below, bromcresol green is yellow, and at pH 5.4 and above it is blue. The method described herein could be used for detecting other organic acids as well.

DETECTOR REAGENT: Bromcresol Green (0.04% in ethanol).

Procedure for Preparing the Detector Reagent

The bromocresol green reagent is available from Aldrich Chemical Company. Transfer 2 ml of the reagent into a 3-ml plastic dropping bottle, replace the tip and screw on the cover.

SOLVENT FOR THE ANALYTE: An organic solvent (e.g. acetone, dichloromethane, hexane)

PREFERRED SOLID SUPPORT: MK6F Silica Gel 60A Glass Backed TLC Sheets, Clifton, N.J.

Analytes Detected with this Test

Methylphosphonic acid (MPA), methylphosphonofluoridic acid (MPFA), ethyl methylphosphonic acid (EMPA), isopropyl methylphosphonic acid (IMPA), pinacolyl methylphosphonic acid (PMPA), cyclohexyl methylphosphonic acid (CMPA), O-ethyl methylphosphonothioic acid (EMPTA). It should be apparent to those skilled in the art that other acids that collect in a small spot when applied in solution to a TLC support, such as organic acids, should be capable of being detected in a similar manner.

Detection Limit for Chemical Weapons Convention Analytes

MPA, EMPA, IMPA, PMPA, CMPA, EMPTA, and MPFA are detectable at the 100 ng level (i.e. when a 1 microliter aliquot of an acetone solution containing 0.01%, or more of analyte is spotted on preferred solid support using a microcapillary tube).

EMPA, IMPA, CMPA, PMPA and EMPTA are also detectable at the 10 ng level (i.e. when a 1 microliter aliquot of a dichloromethane solution containing 0.001% or more of analyte is spotted on the preferred solid support using a microcap).

Equipment and Materials a. Locking forceps or spotting bulb assembly for holding microcap (e.g. cat. # 20-99, Analtech, Newark, Del.)
b. Microcap, 1-microliter (e.g. cat. # 20-01, Analtech)
c. Dropping Bottle, 3-ml capacity, (e.g. cat. # 211630, Wheaton, Millville, N.J.)
d. 0.04% Bromcresol Green in Ethanol, cat. # B-7382, Sigma Chemical Co., St. Louis, Mo.
e. MK6F Silica Gel 60A Glass Backed TLC Sheets or equivalent (e.g. cat. # 4861-1 I0, Whatman Inc., Clifton, N.J.)
f. Acetone (e.g. cat. # GC60032-4, Baxter Healthcare Corp., Burdick and Jackson Div., Muskegon, Mich.)
g. Pencil Procedure 1. Score a 1×3 inch TLC plate into twelve 0.5×0.5 inch sections with a pencil.
2. Lock a 1-microliter microcap in the tip of the locking forceps.
3. Place tip of microcap in a sample of pure acetone (or other solvent for the test) and wait a few seconds for the solvent to be drawn by capillary action to fill the microcap.
4. Place the tip of the microcap in contact with the silica gel surface of the solid support near the center of one of the 0.5×0.5 inch sections. This is the 'control" (analyte level=0) spot.
5. Wait a few seconds for the solvent to evaporate.
6. Using a new microcap, for each sample, spot a different sample solution in each of the remaining 0.5×0.5 inch sections of the plate and allow the solvent to evaporate.
7. Using the dropping bottle, add 1 drop of the bromocresol green to each spot.
8. Observe the plate for the appearance of positive tests. A positive test is indicated by the appearance of a small yellow spot in a large green (wet) or blue (dry) spot. A positive detection signal appears within 1-2 seconds and the colors remain stable for at least several hours.

Purpose and Applications

This micro spot test method is suitable for use as a field test for detecting analytes containing a phosphonic acid group. It provides evidence for or against the presence of chemical weapons convention (or CWC) analytes in a sample.. The test can be used alone or in conjunction with other micro spot tests that detect other functional groups in the sample. When two or more micro spot tests are used in combination, the detection specificity for target chemical weapons convention analyses is increased compared with the result of a single test.

EXAMPLE 2

Micro Spot Test for O-Ethyl Methylphosphonothioic Acid (EMPTA Using 7,7,8, 8-Tetracyanoquinodimethane (TCNO)

Detection Principle

A positive test is the appearance of a blue spot in a larger pale yellow spot. If fresh reagent is not used, however, the reagent spot may be green instead of pale yellow. (With high analyte levels, the center of the blue spot may be bleached so that a white spot appears instead of a blue spot). The control (analyte level=0) and negative tests are indicated by a pale yellow spot that does not contain a blue spot in the center. The color change that is observed in a positive test is due to a sulfhydryl group in the analyte converting the 7,7,8,8-tetracyanoquinodimethane (TCNQ) reagent into a highly colored free radical. In a positive test, the color change occurs within 1 or 2 seconds after applying the TCNQ reagent.

DETECTOR REAGENT: 7,7,8,8-tetracyanoquinodimethane (2.5% in acetone)

Procedure for Preparing Detector Reagent

In a 3-ml plastic dropping bottle place 5 mg of TCNQ. Add 2 ml of acetone. Place the dropping bottle tip in place and screw on the cap. Swirl until all of the TCNQ reagent dissolves.

SOLVENT FOR THE ANALYTE: Acetone, dichloromethane, or hexane.

PREFERRED SOLID SUPPORT: MK6F Silica Gel 60A Glass Backed TLC Sheets, cat.# 4861-110, Whatman Inc.

Analytes Detected with this Test

O-ethyl methylphosphonothioic acid (EMPTA) as well as other materials containing phosphonothioic acid groups, sulfhydryl groups and other TCNQ free radical precursors.

Detection Limits for Chemical Weapons Convention Analytes

EMPTA is detectable at the 10 ng level (i.e. when a 1-microliter aliquot of an acetone solution containing 0.001% or more of analyte is spotted on preferred solid supports using a microcapillary tube).

Equipment and Materials
  same as Example 1 except that 7,7,8,8-Tetracyanoquinodimethane (e.g. cat. # B-7382, Sigma Chemical Co., St. Louis, Mo.) was used instead of the Bromcresol Green.
Procedure
  same as Example 1 except that 7,7,8,8-Tetracyanoquinodimethane was used in step 7. In this example, the observation step required observing the plate for the appearance of positive tests which was indicated by the appearance of a small blue spot in a large yellow spot. The reagent spot may be green if fresh reagent is not used. A positive detection signal appears within 1-2 seconds and the colors remain stable for at least several hours.
Purpose and Applications
  same as in Example 1.

EXAMPLE 3

Micro Spot Test for O-Ethyl Methylphosphonothioic Acid (EMPTA), 1,4-Dithiane, Bis(2-chloroethyl)sulfide (HD), and Bis[2-(2-ethylthio)ethyl]ether (T) Using Gold Chloride and Sodium Hydroxide Detection Principle
  In this test, two detector reagents are added in sequence. The first reagent is an aqueous solution of gold chloride. The second reagent is an aqueous solution of sodium hydroxide. It is believed that the first reagent forms a brown complex with compounds containing a thioether, phosphonothioic acid group or a sulfhydryl group. The second reagent, aqueous sodium hydroxide, probably hydrolyzes the complex thereby forming gold hydroxide, which is unstable, and decomposes to gold oxide. A purplish black spot (gold oxide) in a yellow background signifies a positive test. This color change occurs at the location where the sample was spotted on the solid support. Small black speckles may also appear in the test spot. The small speckles, which occur randomly in the reagent spot should be ignored.
Detector Reagents
1. Aqueous 4% Gold Chloride Solution
2. Aqueous 2N Sodium Hydroxide
Procedure for Preparing Detector Reagents
Reagent #1
  Place hydrogen tetrachloroaurate trihydrate (1 g) in a 25 ml volumetric flask and add water to the mark. Allow the solution to stand for 1 week. Place 2 ml of the solution in 2-ml plastic dropping bottle. Replace the plastic tip and screw the cover on tightly.
Reagent #2
  Place sodium hydroxide (8.0 grams) in a 100 ml volumetric flask. Add approximately 75 ml of water and swirl until the sodium hydroxide dissolves. Allow the solution to cool to room temperature. Add water to the mark.
SOLVENT FOR THE ANALYTE: An organic solvent (e.g. acetone, dichloromethane, hexane)
PREFERRED SOLID SUPPORT: MK6F Silica Gel 60A Glass Backed TLC Sheets, cat. # 4861-110, Whatman Inc.
Analytes Detected with this Test
O-ethyl methylphosphonothioic acid (EMPTA), Bis(2-chloroethyl)sulfide (HD), Bis[2-(2-ethylthiioethyl)]ether (T), 1,4-dithiane and other compounds containing a thioether, a phosphonothioic acid group or a sulfhydryl group.
Detection Limits for Chemical Weapons Convention Analytes
  EMPTA is detectable at the 1 ng level (i.e. when a 1-microliter aliquot of an dichloromethane or hexane solution containing 0.0001% or more of analyte is spotted on the solid support using a microcap).
  Dithiane is detectable at the 10 nanogram level; i.e. when a 1-microliter aliquot of a dichloromethane or hexane solution containing 0.0001% or more of the analyte is spotted on the solid support using a microcap.
  Bis[2-(2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.
Equipment and Materials
  Same as those used in Example 1 except that hydrogen tetrachloroaurate (III) trihydrate (e.g. cat. # 24,459-7, Aldrich Chemical Co.) and sodium hydroxide (#22146-5, Aldrich Chemical Co.) were used instead of the Bromcresol Green.
Procedure
  The same first six steps of example 1 were followed. Thereafter,
  7. Using the dropping bottle, add I drop of the gold chloride reagent to each spot.
  8. Wait two minutes. [EMPTA can be detected down to the 10 ng level at this point. Therefore it can be distinguished from the other analytes (that require base-step 9)].
  9. Using the dropping bottle, add I drop of the sodium hydroxide solution to each spot.
  10. Observe the plate for the appearance of a positive test. A positive test is indicated by the appearance of a small purplish black spot in a large pale yellow spot. A positive detection signal appears within 1–2 seconds and the colors remain stable for at least several hours. The test spot may contain dark speckles that appear randomly and with increasing frequency as the spot ages. These should be ignored.

EXAMPLE 4

Micro Spot Test for Bis(2-chloroethyl)sulfide (HD), Bis[2-(2-ethylthio)ethyl]ether (T), and Other Mustards (Including Nitrogen Mustards) Using 4-(4'-Nitrobenzyl)pyridine and Sodium Hydroxide Detection Principle
  In this test, two detector reagents are used in combination. The first reagent is a 2% solution of 4-(4'-nitrobenzyl)pyridine in an organic solvent such as denatured ethyl alcohol or toluene. The second reagent is an aqueous solution of sodium hydroxide. The thin-layer chromatographic media is heated after the 4-(4'-nitrobenzyl)pyridine is applied to the analyte spot. In the first reaction, heat accelerates the alkylation of 4-(4'-nitrobenzyl)pyridine by the analyte. Basification then results in a deprotonation reaction that produces a blue dye. A positive test response is a small dark blue or purple spot on a white or pale red background.
Detector Reagents
1. 4-(4'-Nitrobenzyl)pyridine (2%) in denatured ethanol (or toluene)
2. Aqueous 2N Sodium Hydroxide
Procedure for Preparing Detector Reagents
Reagent #1
  Place 4-(4'-nitrobenzyl)pyridine (20 mg) in a 2-ml plastic dropping bottle. Add 1 ml of acetone (or toluene). Swirl until the solid dissolves. Replace the plastic tip and screw the cover on tightly.
Reagent #2
  Place sodium hydroxide (8.0 grams) in a 100 ml volumetric flask. Add approximately 75 ml of water and swirl until the sodium hydroxide dissolves. Allow the solution to cool to room temperature. Add water to the mark.
SOLVENT FOR THE ANALYTE: Acetone, dichloromethane, or hexane.
PREFERRED SOLID SUPPORT: MK6F Silica Gel 60A Glass Backed TLC Sheets, cat # 4861-110, Whatman, Inc.
Analytes Detected with this Test
Bis(2-chloroethyl)sulfide (HD), Bis[2-(2-ethylthio)ethyl] ether (T), as well as other sulfur- and nitrogen-mustards. Other alkylating agents (e.g. diethyl sulfate) will also be detected.
Detection Limits for Chemical Weapons Convention Analytes
Bis [2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.
Equipment and Materials
Same as those used in Example 1 except that 4-(4'nitrobenzyl)pyridine (e.g. cat. # N1,420-4, Aldrich Chemical Co.) and sodium hydroxide (#22146-5), Aldrich Chemical Co.) instead of Bromcresol Green.
Procedure
The same first six steps of example 1 were followed. Thereafter, 7. Using a dropping bottle, add 1 drop of the 4-(4'-nitrobenzyl)pyridine reagent.

8. Place the thin-layer chromatographic plate on a hot plate set at 90 degrees Centigrade. Wait for two minutes.

9. Remove the thin-layer chromatographic plate from the hot plate and allow it to cool for 15–30 seconds.

10. Using the dropping bottle, add 1 drop of the sodium hydroxide solution to each spot.

EXAMPLE 5

Micro Spot Test for 4-(Dimethyl)aminopyridine Using Dragendorff Reagent

Detection Principle
A positive test is the appearance of a red spot in a larger orange spot. The color change that is observed in a positive test is due to reaction of 4-(Dimethylamino)pyridine with acetic acid and potassium bismuth iodide (Dragendorff Reagent) to produce a red complex.
Detect or Reagent
Whatman Inc. Catalog No. 4911-107 Dragendorff TLC Visualization Reagent containing potassium iodide and bismuth subnitrate in acetic acid.
Procedure for Preparating the Detector Reagent
Add 2 ml of the detector reagent to a 3-ml dropping bottle. Place the dropping bottle tip in place and screw on the cap.
SOLVENT FOR THE ANALYTE: Acetone, dichloromethane, or hexane:
PREFERRED SOLID SUPPORT: MK6F Silica Gel 60A Glass Backed TLC Sheets, cat #4861-110, Whatman, Inc.
Analytes Detected with this Test
4-(Dimethylamino)pyridine.
Detection Limits for Analytes
4-(Dimethylamino)pyridine is detectable at the 10 ng level (i.e. when a 1 microliter aliquot of an acetone solution containing 0.001 % or more of analyte is spotted on the preferred solid support using a microcapillary tube.
Equipment and Materials
Same as Example 1 except that Dragendorff Reagent (e.g. cat. # 4911-107 from Whatman, Inc., Fairfield, N.J. 07004) was used instead of Bromcresol Green.
Procedure
Same as Example 1 except that Dragendorff Reagent was used in step 7. In this example, the observation step required observing the plate for the appearance of positive tests which was indicated by the appearance of a small red spot in a large orange spot. A positive detection signal appears within 1 minute and the colors remain stable at least for several hours.
Purpose and Applications
This micro spot test is suitable as a test for detecting analytes such as 4-(dimethylamino)pyridine, quaternary nitrogen compounds, and alkaloids.

As a further example, the invention has applicability for urine and drug testing and as a supplement to commercially available thin layer chromatographic (TLC) test kits. One such test kit has been marketed by Eastman Kodak Co. (Cat. No. 13125 Kodak Chromat/O/Screen 60 Analysis Kit for Alkaloids). With this kit, the tests are performed by spotting a TLC strip, eluting the strip with a solvent, and then detecting the substances present by spraying the TLC strip with a chromogenic reagent. The appearance of a spot of a particular color indicates the presence of an alkaloid. Using the Chromat/O/Screen TLC kit as an example, the kit could be designed to use the microspot tests of the present invention as a means for rapidly prescreening a large number of samples. The microspot tests would be performed simply by spotting the analyte solution several times using a microcap each time on a different TLC strip, and then adding a drop of chromogenic detector reagent to each spot. Different chromogenic reagents would be used for each class of chemicals that are of interest. Compared with conventional TLC methods, the microspot test methodology of the present invention would result in increased sample throughput and much higher sensitivity of detection. Throughput would be increased because the time consuming elution step conventional with TLC tests, would not be needed, and samples that did not provide any positive responses in the microspot tests would be quickly eliminated from further consideration If necessary, it would still be possible to use more time consuming TLC methods, but there would be a need to test only those samples that gave a positive test.

REFERENCES

Detector Reagents

1. Jungreis, E., Spot Test Analysis: Clinical, Environmental, Forensic, and Geochemical Applications, Chemical Analysis, Volume 141, Second Edition, John Wiley and Sons, Inc., NY, 1997.
2. Mohammad, A., and Tiwari, S., Thirty-Five Years of Thin-Layer Chromatography in the Analysis of Inorganic Anions, Separation Science and Technology, 30(19), 3577–3614 (1995).
3. Jork, Helmut, Editor, Thin-Layer Chromatography: Reagents and Detection Methods, Vol. 1b, Physical and Chemical Detection Methods, John Wiley & Sons, NY, 1994.
4. Green, F. J., The Sigma Aldrich Handbook of Stains, Dyes, and Indicators, Aldrich Chemical Co., 1990.
5. Novak, T. J., and Davis, P. M., Detection of Sulfur Mustards Using Spectrofluorometry, U.S. Pat. No. 5,032,380, Jul. 16, 1991.
6. Jork, Helmut, Editor, Thin-Layer Chromatography: Reagents and Detection Methods, Vol. 1a, Physical and Chemical Detection Methods, John Wiley & Sons, NY, 1989.
7. Novak, T. J., 4,4'-Dithiodianil, U.S. Pat. No. 4,414,414, Nov. 8, 1983.

8. Sherma, J., Practice and Applications of Thin Layer Chromatography on Whatman KC$_8$Reversed Phase Plates, TLC Technical Series, Volume 1 (1981), Whatman Inc., Clifton, N.J. 07014.
9. Sass, S., and Ludemann, W., J. of Chromatography, 187, 447–452 (1980).
10. Gasparic, J., and Churacek, J., Detection Reagents, Laboratory Handbook of Paper and Thin Layer Chromatography, pp 323–335, Ellis Horwood, Ltd, England, 1978.
11. Corporate Authors, E. Merck, Dyeing Reagents for Thin Layer and Paper Chromatography, E. Merck, Darmstadt, Federal Republic of Germany, 1975.
12. Corporate Authors, Eastman Kodak Company, Eastman TLC Visualization Reagents =and Chromatographic Solvents, Kodak Publication No. JJ-5 (1973), Eastman Kodak Company, Rochester, N.Y. 14650.
13. Zweig, G., and Sherma, J., Editors, Detection Reagents for Paper and Thin-Layer Chromatography, CRC Handbook of Chromatography, Volume II, Section II.1, pp 103–189, CRC Press, 1972.
14. Sawicki, E., Engel, C. R., and Elbert, W. C., Talanta 14, 1169–1178 (1967).
15. Ruch, W. E., Editor, Chemical Detection of Gaseous Pollutants: An Annotated Bibliography, Ann Arbor Science Publishers, Inc., Ann Arbor, Mich., 1966.
16. Feigl, F., Spot Tests in Organic Analysis, 6th Edition, Elsevier Science, Ltd., 1966.
17. Bryant, F., Overell, B. T., Biochim et Biophys. Acta 10, 471–6 (1963).
18. Feigl, F., Spot Tests in Inorganic Analysis, 7th Edition, Elsevier Science, Ltd, 1958.
19. Epstein, J., Rosenthal, R. W., and Ess, R. J., Anal. Chem. 27, 1435–39 (1955).
20. Bregoff, H. M., Roberts, E., Delwiche, C. C., J. Biol. Chem. 205, 565 (1953).
21. Munier, R. Bull. Soc. Chim. Biol. 35, 1225 (1953).
22. Obermiller, M., Angew. Chem. 49, 162–164 (1936).
23. Witten, B., and Prostak, A., Sensitive Detector Crayons for Phosgene, Hydrogen Cyanide, and Lewisite, Anal. Chem. 29, 885–7 (1957).
24. Pheil, R. W., Crayon for the Detection of G-Agents, U.S. Pat. No. 2,929, 791, Mar. 22, 1960.
25. Sass, S., Ludemann, W. D., Witten, B., Fischer, V., Sisti, A. J., and Miller, J. I., Colorimetric Determination of Certain Organophosphorus Compounds and Acylating Agents—Use of Diisonitrosoacetone Reagent, Anal. Chem. 29, 1346–9 (1957).
26. Kramer, D. N., and Morin, R. D., Detection of G-Agents, U.S. Pat. No. 2,926,072, Feb. 23, 1960.
27. Gehauf, B., Epstein, J., Wilson, G. B., Witten, B., Sass, S., Bauer, V. E., Rueggeberg, W. H. C., Anal. Chem. 29,276 (1957).
28. Gehauf, B., and Goldenson, J., Detection and Estimation of Nerve Gases by Fluorescence Reaction, Anal. Chem. 29, 276 (1957).
29. Brante, G., Iodine as a Means of Development in Paper Chromatography, Nature 163, 651–2 (1949).
30. Sokolowski, M., and Rozylo, J. K., TLC Analysis of Warfare Agents under Battlefield Conditions, Journal of Planar Chromatography 6, 467–71 (1993).
31. Munavalli, S., and Pannella, M., Thin-Layer Chromatography of Mustard and Its Metablolites, Journal of Chromatog., 437, 423–8 (1988).
32. Ellman, G. H., Arch. Biochem. Biophys., 82, 70–77 (1959).
33. Mikrochim Acta, 788 (1971); Ibid., 341 (1973).
34. Mikrochim Acta, 526 (1972).
35. Chemical and Engineering News, pg 29, Aug. 1, 1994.
36. Yoe, J. H., and Sarver, L. A., Organic Analytical Reagents, John Wiley, NY, 1941, pages 66–326.
37. Maile, R. J., Fishesser, G. J., and Anderson, M. M., Thin-Layer Chromatography of Phosphonic Acid Derivatives, Journal of Chromatog. 132, 366–68 (1977).
38. Reiner, M., ed. , Standard Methods of Clinical Chemistry, Vol. 1, Academic Press, NY, 1953, page 84.

What is claimed is:

1. A method of detecting the presence of an analyte wherein the analyte remains at the spot of application and is analyzed at this same spot, comprising the steps of:

placing the analyte in a solution where the solvent for the analyte consists of a non-aqueous solvent selected from the group of dimethylsulfoxide, N-methylpyrrolidone, N,N-dimethyl acetamaide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane;

placing the solution containing the analyte in a tube having an end portion with a microcapillary sized opening, so that when the tube is placed in contact with a chromatographic sheet having a surface layer formed of sorbent material selected from the group consisting of silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents, the solution containing the analyte is withdrawn from the end portion of the tube and onto the surface layer of the sorbent material by capillary action;

placing the end portion of the tube having the microcapillary sized opening in contact with the sorbent material so the solution is withdrawn from the tube by capillary action, the solvent being absorbed into the sorbent material and the analyte being separated from the solvent and adsorbed by the sorbent material at the place of contact of the end portion of the tube with the sorbent material; and placing a chromogenic detector reagent for the analyte on the sorbent material at the place of contact of the end portion of the tube with the sorbent material to detect the presence of the analyte separated from the solvent and concentrated in the sorbent material at the place of contact of the end portion of the tube with the sorbent material, whereby a chromogenic indicator is formed when the analyte is present in the sorbent material.

2. A method of screening a solution for an analyte that has been dissolved in a solvent to form the solution and for detecting the presence of the analyte when the solution is deposited in a surface layer of a sorbent material wherein the analyte remains at the spot of application and is analyzed at this same spot comprising the steps of:

placing the solution containing the analyte in a tube having an end portion forming a microcapillary sized opening in the end portion of the tube so that when the tube is placed in contact with the sorbent material, the solution containing the analyte in the tube is withdrawn from the end portion of the tube and into the sorbent material by capillary action;

placing the end portion of the tube forming the microcapillary sized opening in contact with the sorbent material so that the solution is withdrawn from the tube by capillary action, the solvent being absorbed into the sorbent material and the analyte being separated from the solvent and adsorbed by the sorbent material at the point of contact of the end portion of the tube with the sorbent material; and placing a detector reagent for the analyte on the sorbent material at the place of contact of the end portion of the tube with the sorbent material to detect the presence of the analyte separated from the solvent and concentrated in the sorbent material at the place of contact of the end portion of the tube with the sorbent material.

3. The method of claim 2, wherein the diameter of the microcapillary sized opening has range of diameters of from about 0.05 to about 1.6 millimeters so that when the end portion of the tube is placed in contact with the sorbent material, the solution containing the analyte is withdrawn from the end portion of the tube by capillary action, separated from the solvent at the place where the end portion of the tube having the microcapillary opening contacts the sorbent material and adsorbed by the sorbent material.

4. The method of claim 2, wherein the sorbent material is formed of a polar material selected from the group consisting of silica gel, high performance thin layer chromatography (HPTLC) silica gel, polysilicic acid, and aluminum oxide and the solvent for the analyte is a non-aqueous solvent that is less polar than the sorbent material and selected from the group of acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, isohexanes, hexane, heptane, cyclopentane, trichlorotrifluoroethane, and pentane.

5. The method of claim 2, wherein the sorbent material comprises a thin layer chromatographic sheet having a surface layer of silica gel sorbent material and the solvent for the analyte is selected from the group consisting of acetone, dichloromethane, toluene, o-xylene, m-xylene, p-xylene, n-butyl chloride, cyclohexane, trimethylpentane, petroleum ether, heptane, cyclopentane, pentane and hexane.

6. The method of claim 2, further comprising the step of dissolving the detector reagent in a detector reagent solvent to form a detector reagent solution prior to the step of placing the detector reagent for the analyte on the sorbent material at the place of contact of the end portion of the tube with the sorbent material and to indicate the presence of the analyte separated from the solvent and concentrated in the sorbent material at the place of contact of the end portion of the tube with the sorbent material.

7. The method of claim 6, wherein the sorbent material is a polar material selected from the group of silica gel, high performance thin layer chromatography (HPTLC) silica gel, polysilicic acid, aluminum oxide, cellulose, and polyamide, and the solvent for the analyte is selected from solvents having less polarity than the sorbent material and selected from the group consisting of acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, isohexanes, hexane, heptane, cyclopentane, trichlorotrifluoroethane, and pentane.

8. The method of claim 6, wherein the sorbent material is a chromatographic material selected from the group consisting of silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents and the solvent for the analyte is selected from the group consisting of acetic acid, water, aqueous buffer solution with a pH in the range 2-12, dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, isohexanes, hexane, heptane, cyclopentane, trichlorotrifluoroethane, and pentane.

9. The method of claim 6, wherein the detector reagent is selected from the group consisting of bromcresol green; 7,7,8,8-tetracyanoquinodimethane (TCNQ); gold chloride; gold chloride/NaOH solution; 4-(4'-nitrobenzyl)pyridine/NaOH; cholinesterase/indoxyl acetate; sodium pyrophosphate peroxide/aromatic amine; potassium bismuth iodide; 1,3-diisonitrosoacetone guanidinium salt; bis(diethylamino) benzophenone oxime; bis(diethylamino)benzophenone; bis (dimethylamino)thiobenzophenone; phenylazoformic acid 2-diphenylhydrazide; diphenylcarbazone; diphenylthiocarbazone; mercuric salt; diethyldithiocarbamic acid silver salt;

2,2'-dithiobis(5-nitropyridine); 5,5'-dithiobis(2-nitrobenzoic acid), Ellman's Reagent; molybdenum oxide in sulfuric acid; ammonium molybdate; iodine/starch; and sulfuric acid (4M); ammonium sulfate; ammonium cerium(IV)sulfate; ammonium iron(II)sulfate; cobalt(II)thiocyanate; palladium (II)chloride; potassium iodide plateate; sodium tetraphenyl boron; o-tolidine; and N,2,6-trichloro-p-benzoquinoneimine.

10. The method of claim 9, wherein the solvent for the detector reagent has less polarity than the sorbent material.

11. The method of claim 2, wherein sorbent material is formed of a chromatographic polar material and the solvent for the analyte is a non-aqueous solvent that has a lower polarity than the sorbent material.

12. The method of claim 2, further comprising the step of dissolving the detector reagent in a detector reagent solvent to form a detector reagent solution prior to the step of placing the detector reagent for the analyte on the sorbent material, wherein the sorbent material is a polar chromatographic material and the solvents for the analyte and the detector reagents have less polarity than the sorbent material.

13. The method of claim 2, wherein the sorbent material is formed of a non-polar material selected from the group of reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, and Kieselghur impregnated with hydrocarbons and the solvent for the analyte is an aqueous solvent mixture containing solvents from the group comprising water, methanol, N,N-dimethylformamide, acetonitrile, acetic acid, acetone, pyridine, ethanol, dioxane, chloroform, isopropanol, ethyl acetate, tetrahydrofuran, and n-propanol.

14. The method of claim 2, wherein the sorbent material is formed of an ion-exchange material selected from the group of anion exchange resin, cation exchange resin and diethylaminoethylcellulose and the solvent for the analyte comprises water.

15. A method of detecting the presence of an analyte wherein the analyte remains at the spot of application and is analyzed at this same spot, comprising the steps of:
placing a detector reagent for the analyte on a chromatographic layer of a sorbent material selected from the group consisting of silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, and diethylaminoethyl cellulose;
placing the analyte in a solution where the solvent for the analyte is selected from the group of acetic acid, water, aqueous buffer solution with a pH in the range 2-12, dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane;
placing the solution containing the analyte in a tube having an end portion formed with a microcapillary sized opening, so that when the tube is placed in contact with the sorbent material, the solution containing the analyte is withdrawn from the end portion of the tube and into the sorbent material by capillary action;
placing the end portion of the tube having the microcapillary sized opening in contact with the sorbent material at the spot where the detector reagent has been deposited on the sorbent layer so the solution is withdrawn from the tube by capillary action with the solvent being absorbed into the sorbent material and the analyte being separated from the solvent and adsorbed into the sorbent material at the point of contact of the end portion of the tube with the sorbent material, whereby a chromogenic indicator is formed when the analyte is present in the sorbent material.

16. A method of detecting the presence of an analyte in a solvent solution where the solution is deposited on a selected sorbent material by capillary action to cause the analyte to remain concentrated at the spot of deposition on the sorbent material wherein the analyte is analyzed at the same spot comprising the steps of:
placing the analyte in a solution where the solvent for the analyte consists of a non-aqueous solvent selected from the group of dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane;
placing the solution containing the analyte in a microcapillary sized tube having a volume of from about 0.1 to about 30.0 microliters and having an end portion with a microcapillary sized opening having a diameter of from about 0.05 to about 1.6 millimeters so that when the tube is placed in contact with a chromatographic sheet having a surface layer formed of sorbent material selected from the group consisting of silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents, the solution containing the analyte is withdrawn from the end portion of the tube and onto the surface layer of the sorbent material by capillary action;

placing the end portion of the tube having the microcapillary sized opening in contact with the sorbent material so the solution is withdrawn from the tube by capillary action, the solvent being absorbed into the sorbent material and the analyte being separated from the solvent and the analyte being concentrated and fixed at the point contact of the end portion of the tube with the sorbent material; and placing a chromogenic detector reagent for the analyte on the sorbent material at the point of contact of the end portion of the tube with the sorbent material to detect the presence of the analyte that is concentrated in the sorbent material at the point of contact of the end portion of the tube with the sorbent material, whereby a chromogenic indicator is formed when the analyte is present in the sorbent material.

* * * * *